(12) United States Patent
Rampersad et al.

(10) Patent No.: US 7,290,396 B2
(45) Date of Patent: *Nov. 6, 2007

(54) CRYOGENIC BIOLOGICAL PRESERVATION UNIT

(75) Inventors: Bryce Mark Rampersad, Cheektowaga, NY (US); John Henri Royal, Grand Island, NY (US); Barry Minbiole, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 359 days.

This patent is subject to a terminal disclaimer.

(21) Appl. No.: 11/037,097

(22) Filed: Jan. 19, 2005

(65) Prior Publication Data

US 2006/0156740 A1    Jul. 20, 2006

(51) Int. Cl.
*F25B 9/00* (2006.01)
*F25B 19/00* (2006.01)
*F17C 13/00* (2006.01)
*F25D 11/00* (2006.01)

(52) U.S. Cl. ............... 62/6; 62/51.1; 62/457.9; 62/440

(58) Field of Classification Search ............ 62/6, 62/51.1, 457.9, 440
See application file for complete search history.

(56) References Cited

U.S. PATENT DOCUMENTS

| | | | |
|---|---|---|---|
| 4,300,356 A | 11/1981 | Notaro et al. ............ 62/50 |
| 4,489,569 A * | 12/1984 | Sitte ....................... 62/49.2 |
| 6,076,372 A | 6/2000 | Acharya et al. ............ 62/606 |
| 6,128,914 A | 10/2000 | Tamaoki et al. ............ 62/440 |
| 6,205,794 B1 | 3/2001 | Brothers .................. 62/51.1 |
| 6,226,997 B1 * | 5/2001 | Vago ...................... 62/130 |
| 6,327,865 B1 | 12/2001 | Bonaquist et al. ............ 62/79 |
| 6,397,620 B1 | 6/2002 | Kelly et al. ............... 62/275 |
| 6,426,019 B1 | 7/2002 | Acharya et al. ............ 252/67 |
| 6,430,938 B1 | 8/2002 | Royal et al. ................. 62/6 |
| 6,564,120 B1 * | 5/2003 | Richard et al. ............ 700/214 |
| 6,640,552 B1 | 11/2003 | Rampersad et al. ........... 62/6 |
| 2005/0061006 A1 * | 3/2005 | Bonaquist et al. ............ 62/6 |
| 2005/0069861 A1 * | 3/2005 | Zimmermann et al. ...... 435/1.1 |
| 2006/0260328 A1 * | 11/2006 | Rampersad .................. 62/6 |
| 2006/0260329 A1 * | 11/2006 | Rampersade et al. .......... 62/6 |
| 2007/0000258 A1 * | 1/2007 | Bonaquist et al. ............ 62/6 |
| 2007/0033952 A1 * | 2/2007 | Rampersad et al. ........... 62/6 |

* cited by examiner

*Primary Examiner*—William C Doerrler
(74) *Attorney, Agent, or Firm*—David M. Rosenblum

(57) ABSTRACT

A cryogenic biological preservation unit having a removable lid and an integrated cryocooler positioned apart from, or within a fixed portion of, the lid and which provides refrigeration to the upper portion of the interior of the unit which also contains a pool of liquid cryogen and at least one biological sample preferably positioned above the pool of liquid cryogen.

9 Claims, 2 Drawing Sheets

CRYOGENIC BIOLOGICAL PRESERVATION UNIT

TECHNICAL FIELD

This invention relates generally to preservation of biological samples and, more particularly, to preservation of biological samples at cryogenic temperatures.

BACKGROUND ART

There is a growing trend toward cryogenic storage of biological samples at temperatures below 140K. This trend is driven by the fact that little to no sample degradation occurs below the sample glass transition temperature which is about 140K. Conventional cryogenic biological sample preservation units that store biological samples at temperatures below 140K use liquid cryogen, such as liquid nitrogen, to keep the biological samples cold. These units typically store the samples within a vacuum insulated space above a pool of liquid cryogen or immersed within the pool of liquid cryogen. The liquid cryogen needs to be periodically replenished. This is costly, not only because of the cost of the cryogen, but also because of the complicated procedures required to handle the liquid cryogen.

SUMMARY OF THE INVENTION

One aspect of the invention is:

A cryogenic biological preservation unit comprising:

(A) an insulated vessel having a vessel interior, and a lid having a fixed portion and a removable portion, said lid positioned within an opening allowing access to the vessel interior;

(B) a pool of liquid cryogen within the vessel interior, and at least one biological sample within the vessel interior; and (C) a cryocooler having cold finger, said cold finger penetrating at least in part the fixed portion of the lid, and positioned to provide refrigeration to the vessel interior.

Another aspect of the invention is:

A cryogenic biological preservation unit comprising:

(A) an insulated vessel having a vessel interior, and a lid positioned within an opening allowing access to the vessel interior;

(B) a pool of liquid cryogen within the vessel interior, and at least one biological sample within the vessel interior; and (C) a cryocooler having a cold head with a cold finger, said cold head positioned apart from the lid with the cold finger positioned to provide refrigeration to the vessel interior.

As used herein the term "cryocooler" means a refrigerator which can produce refrigeration below 193K for the purpose of cooling biological samples.

As used herein the term "cold head" means the portion of the cryocooler containing the cold heat exchanger, aftercooler and regenerator.

As used herein the term "cold finger" means a portion of a cold head that is configured such that the cold heat exchanger is located at one end of the cooled head. The cold finger refers to the portion of the cold head with this configuration that, in operation, is at a temperature below that of the aftercooler.

As used herein the term "biological sample" means an organic material. Some examples of biological samples are proteins, blood platelets, cartilage and heart valves.

DETAILED DESCRIPTION

Figure 1:
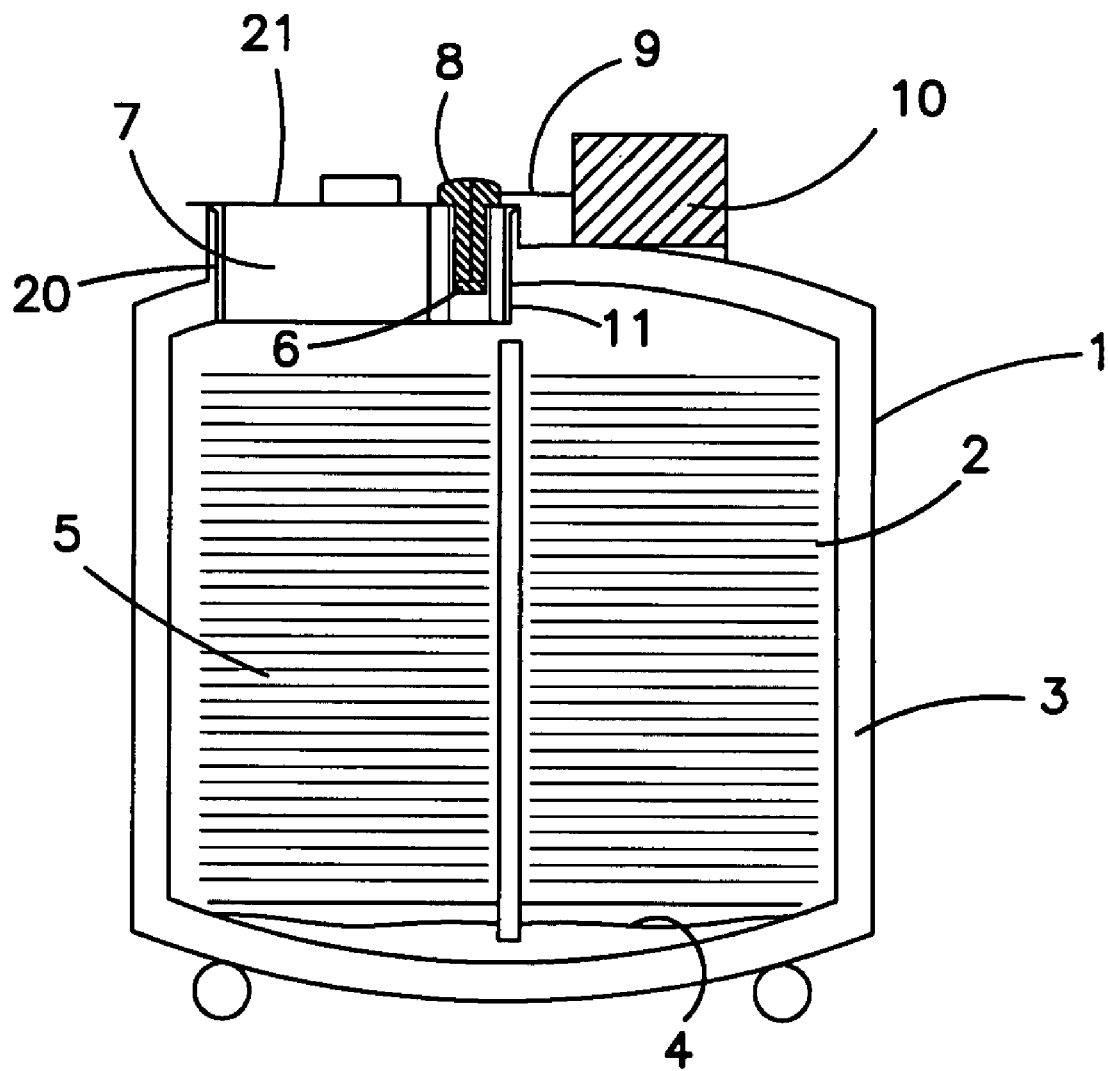
FIG. 1 is a cross sectional representation of one preferred embodiment of the cryogenic biological preservation unit of this invention wherein the lid has a fixed portion and a removable portion and the cryocooler cold finger penetrates at least in part the fixed portion of the lid.

The invention will be described in detail with reference to the Drawings. Referring now to FIG. 1, there is shown a cryogenic biological preservation unit having a vessel wall 1 and having insulation, typically vacuum insulation, 3 adjacent the inside of vessel wall 1. Vessel wall 1 and insulation 3 define the vessel interior or storage space 2. In the lower portion of vessel interior 2 is a pool of liquid cryogen 4. Generally and preferably the liquid cryogen comprises liquid nitrogen. Other liquid cryogens may be used in the practice of the invention provided that they have a normal boiling point below 193K.

Within vessel interior 2 and preferably above liquid cryogen pool 4 there is stored at least one biological sample. In FIG. 1 there is illustrated in representational form a plurality of biological samples 5 on a rack system. In general the cryogenic biological preservation unit of this invention will have a diameter within the range of from 30 to 60 inches and a height within the range of from 45 to 75 inches. Depending upon the size of the biological samples and upon the type of rack system used, the cryogenic biological preservation unit of this invention can accommodate or store up to 15,000 to 80,000 biological samples in 1-2 ml plastic vials. Large items such as blood bags and organs can also be stored.

The cryogenic biological preservation unit of this invention has an opening 20 which allows access to the vessel interior 2 from outside the vessel and through which biological samples are put into and removed from the vessel interior. Within opening 20 there is positioned lid 21 which is typically insulated using a closed cell foam such as expanded polystyrene, and which is positioned in opening 20 when access to vessel interior 2 is not desired. In the embodiment of the invention illustrated in FIG. 1, lid 20 comprises a fixed portion 11 and a removable portion 7. The removable portion 7 is removed from opening 20 when access to vessel interior 2 is desired.

Any suitable cryocooler may be used in the practice of this invention. Among such cryocoolers one can name Stirling cryocoolers, Gifford-McMahon cryocoolers and pulse tube refrigerators. A pulse tube refrigerator is a closed refrigeration system that oscillates a working gas in a closed cycle and in so doing transfers a heat load from a cold section to a hot section. The frequency and phasing of the oscillations is determined by the configuration of the system. The driver or pressure wave generator may be a piston or some other mechanical compression device, or an acoustic or thermoacoustic wave generation device, or any other suitable device for providing a pulse or compression wave to a working gas. That is, the pressure wave generator delivers energy to the working gas within the pulse tube causing pressure and velocity oscillations. Helium is the preferred working gas; however any effective working gas may be used in the pulse tube refrigerator and among such one can name nitrogen, oxygen, argon and neon or mixtures containing one or more thereof such as air.

The oscillating working gas is preferably cooled in an aftercooler and then in a regenerator as it moves toward the cold end. The geometry and pulsing configuration of the pulse tube refrigeration system is such that the oscillating working gas in the cold head expands for some fraction of the pulsing cycle and heat is absorbed by the working gas by indirect heat exchange which provides refrigeration to the vessel interior. Preferably the pulse tube refrigeration system employs an inertance tube and reservoir to maintain the gas displacement and pressure pulses in appropriate phases. The size of the reservoir is sufficiently large so that essentially very little pressure oscillation occurs in it during the oscillating flow.

The cryocooler components 10 include the mechanical compression equipment (pressure wave generator), the inertance tube and reservoir, the final heat rejection system and the electrical components required to drive and control the cryocooler. Electrical energy is primarily converted into acoustic energy in the pressure wave generator. This acoustic energy is transferred by the oscillating working gas to the cold head 8 via the transfer tube 9. The transfer tube 9 connects the pressure wave generator to the aftercooler located at the warm end of the cold head 8, where heat is removed as previously described. The cryocooler can be controlled to provide varying amounts of refrigeration to the cold end of the cold finger 6 depending on the conditions in the cryogenic biological preservations unit vessel interior 2. This is accomplished by modulating the acoustic power output from the pressure wave generator by varying the voltage and thus the electrical power supplied. The cryocooler would preferably be controlled based on the temperature of the vessel interior 2 of the cryogenic biological preservation unit.

In the embodiment of the invention illustrated in FIG. 1, cold finger 6 penetrates into vessel interior 2 and provides refrigeration directly to the vessel interior. The refrigeration cools and condenses cryogen vapor within the upper portion of the vessel interior 2 thus significantly reducing the need to replenish the liquid cryogen from outside the unit and thereby minimizing costly and complicated cryogen handling procedures and systems. The condensed cryogen falls by gravity or is directed back to the liquid cryogen pool in the lower portion of the vessel interior.

The temperature at the lowest level of the sample storage within the vessel interior maybe as low as 77K and is generally within the range of from 80 to 95K. However, the normal temperature at the upper levels of the sample storage may be within the range of from 95 to 140K without the use of the integrated cryocooler of this invention. Samples in the top racks of conventional cryogenic biological preservation units could exceed the glass transition temperature of the biological samples when the lid is removed for access to the interior. For this reason, storage of biological samples in the upper portion of conventional cryogenic biological preservation units is often avoided. However, with the cryogenic biological preservation unit of this invention which provides cryocooler refrigeration to the upper portion of the vessel interior, biological samples may be stored in the upper portion of the vessel interior without fear of degradation due to elevated temperature. This increases the effective capacity of the unit which is another advantage of the cryogenic biological preservation unit of this invention over conventional systems.

Figure 2:
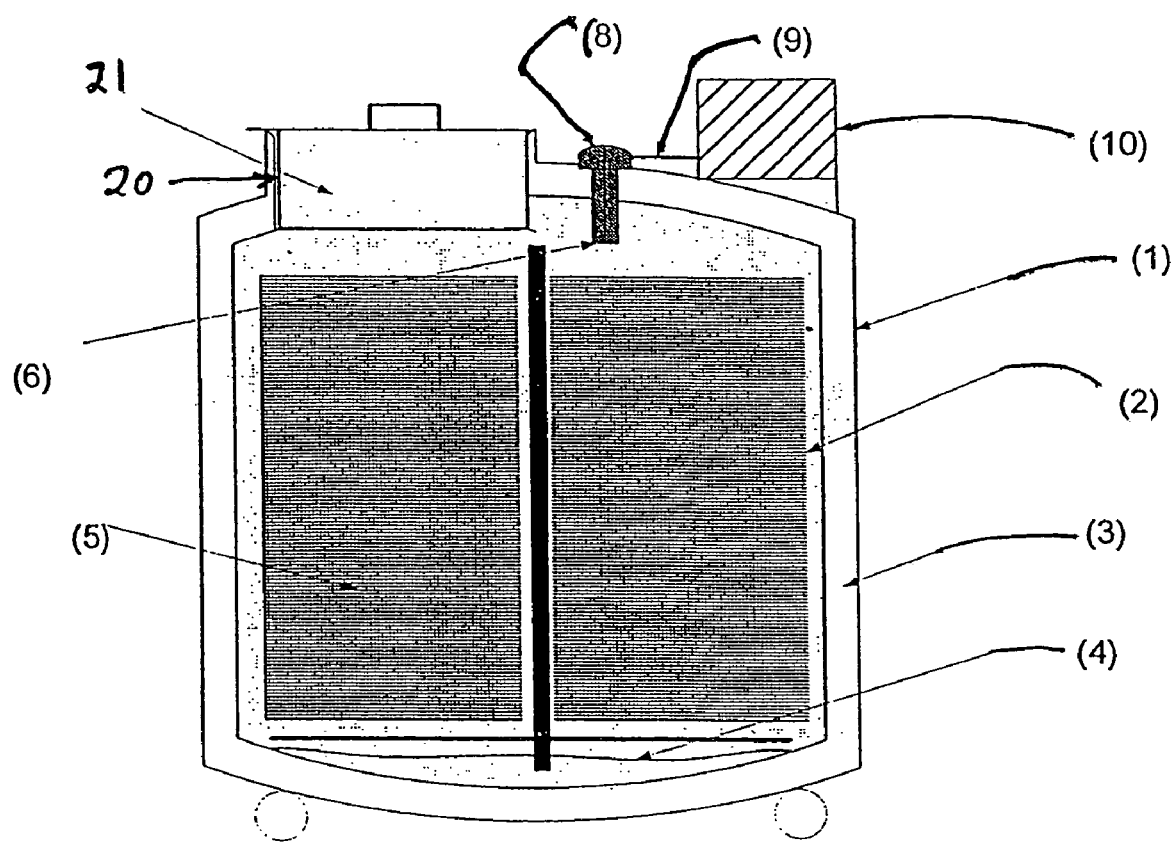
FIG. 2 is a cross sectional representation of another preferred embodiment of the cryogenic biological preservation unit of this invention wherein the cryocooler cold head is positioned apart from the lid.

FIG. 2 illustrates another embodiment of the cryogenic biological preservation unit of this invention. The numerals of FIG. 2 are the same as those of FIG. 1 for the common elements, and these common elements will not be described again in detail. In the embodiment of the invention illustrated in FIG. 2, the lid 21 is comprised entirely of a removable part and the cryocooler cold head 8 is positioned apart from the lid. The cold finger 6 penetrates into the vessel so as to provide refrigeration directly to the vessel interior 2. Alternatively, the cryocooler cold finger could be positioned so that it does not penetrate into the vessel interior but rather provides refrigeration to the inner vessel wall and thus indirectly to the vessel interior.

Although the invention has been described in detail with reference to certain preferred embodiments, those skilled in the art will recognize that there are other embodiments of the invention within the spirit and the scope of the claims.

The invention claimed is:

1. A cryogenic biological preservation unit comprising:
   (A) an insulated vessel having a vessel interior, and a lid having a fixed portion and a removable portion, said lid positioned within an opening allowing access to the vessel interior;
   (B) a pool of liquid cryogen within the vessel interior, and at least one biological sample within the vessel interior; and
   (C) a cryocooler having a cold finger, said finger penetrating at least in part the fixed portion of the lid, and positioned to provide refrigeration to the vessel interior.

2. The cryogenic biological preservation unit of claim 1 wherein the liquid cryogen comprises liquid nitrogen.

3. The cryogenic biological preservation unit of claim 1 wherein the cryocooler is a pulse tube refrigerator.

4. The cryogenic biological preservation unit of claim 1 wherein said at least one biological sample is above the pool of liquid cryogen.

5. A cryogenic biological preservation unit comprising:
   (A) an insulated vessel having a vessel interior, and a lid positioned within an opening allowing access to the vessel interior;
   (B) a pool of liquid cryogen within the vessel interior, and at least one biological sample within the vessel interior; and
   (C) a cryocooler having a cold head with a cold finger, said cold head positioned apart from the lid with the cold finger positioned to provide refrigeration to the vessel interior.

6. The cryogenic biological preservation unit of claim 5 wherein the liquid cryogen comprises liquid nitrogen.

7. The cryogenic biological preservation unit of claim 5 wherein the cryocooler is a pulse tube refrigerator.

8. The cryogenic biological preservation unit of claim 5 wherein the cold finger penetrates into the vessel interior.

9. The cryogenic biological preservation unit of claim 5 wherein said at least one biological sample is above the pool of liquid cryogen.

* * * * *